(12) United States Patent
Braun et al.

(10) Patent No.: US 9,220,335 B2
(45) Date of Patent: Dec. 29, 2015

(54) TOOTHBRUSH HEAD

(71) Applicant: The Gillette Company, Boston, MA (US)

(72) Inventors: Phillip Maurice Braun, Exeter, RI (US); William Ralph Brown, Jr., Peabody, MA (US); Thomas Aurele Christman, Lexington, MA (US); Thomas Craig Masterman, Brookline, MA (US); Karen Lynn Claire-Zimmet, Kronberg (DE); Ronald Richard Duff, Jr., Shrewsbury, MA (US)

(73) Assignee: The Gillette Company, Cincinnati, OH (US)

( * ) Notice: Subject to any disclaimer, the term of this patent is extended or adjusted under 35 U.S.C. 154(b) by 0 days.

(21) Appl. No.: 14/053,705

(22) Filed: Oct. 15, 2013

(65) Prior Publication Data
US 2014/0033458 A1    Feb. 6, 2014

Related U.S. Application Data

(63) Continuation of application No. 12/186,639, filed on Aug. 6, 2008, now abandoned, which is a continuation of application No. 11/825,387, filed on Jul. 6, 2007, now Pat. No. 7,975,344, which is a continuation of application No. 11/799,733, filed on May 2, 2007, now abandoned, which is a continuation of application No. 10/389,448, filed on Mar. 14, 2003, now abandoned.

(51) Int. Cl.
*A46B 9/12*    (2006.01)
*A46B 9/04*    (2006.01)
(Continued)

(52) U.S. Cl.
CPC ... *A46B 9/04* (2013.01); *A46B 3/16* (2013.01); *A46B 5/002* (2013.01); *A46B 5/0025* (2013.01); *A46B 7/06* (2013.01); *A46B 9/025* (2013.01); *A46B 9/06* (2013.01); *A61C 17/3481* (2013.01); *B29C 45/0055* (2013.01); *A46B 9/12* (2013.01); *A46B 2200/1066* (2013.01); *B29L 2031/425* (2013.01)

(58) Field of Classification Search
CPC .................................................. A46B 2200/1006
USPC ................................. 15/167.1, 193, 110, 186
See application file for complete search history.

(56) References Cited

U.S. PATENT DOCUMENTS

| 301,644 A | 7/1884 | Thompson |
|---|---|---|
| 429,839 A | 6/1890 | Beissbarth |

(Continued)

FOREIGN PATENT DOCUMENTS

| AU | 44639693 | 8/1993 |
|---|---|---|
| CA | 454913 | 3/1949 |

(Continued)

OTHER PUBLICATIONS

Board Opinion from the Chinese Patent Office with regard to Application No. 01806615.1 dated Jul. 17, 2007 with translation.

(Continued)

*Primary Examiner* — Laura C Guidotti
(74) *Attorney, Agent, or Firm* — Alexandra S. Anoff

(57) ABSTRACT

A toothbrush head having a top surface and a bottom surface opposite the top surface is described herein. The head has a first portion, a second portion, and an opening between the first portion and the second portion. The opening extends from the top surface to the bottom surface. A first plurality of contact elements are positioned on the first portion and the second portion. A second plurality of contact elements are positioned on the first portion and the second portion. Each of the second plurality of contact elements has an elastomer.

14 Claims, 10 Drawing Sheets

(51) Int. Cl.
  *A46B 3/16*       (2006.01)
  *A46B 5/00*       (2006.01)
  *A46B 7/06*       (2006.01)
  *A46B 9/02*       (2006.01)
  *A46B 9/06*       (2006.01)
  *A61C 17/34*      (2006.01)
  *B29C 45/00*      (2006.01)
  *B29L 31/42*      (2006.01)

(56) References Cited

U.S. PATENT DOCUMENTS

| | | |
|---|---|---|
| 601,405 A | 3/1898 | Shepherd |
| 819,444 A | 5/1906 | Monroe |
| 1,022,920 A | 4/1912 | Anderson |
| 1,063,523 A | 6/1913 | Farrar |
| 1,128,139 A | 2/1915 | Hoffman |
| 1,142,698 A | 6/1915 | Grove et al. |
| 1,172,109 A | 2/1916 | Cammack |
| 1,191,556 A | 7/1916 | Blake |
| 1,268,544 A | 12/1916 | Cates |
| 1,251,250 A | 12/1917 | Libby |
| 1,323,042 A | 11/1919 | Gardner |
| 1,526,267 A | 9/1924 | Dessau |
| 1,673,638 A | 6/1928 | Peterson |
| 1,693,229 A | 11/1928 | Felmar |
| 1,698,128 A | 1/1929 | Funk |
| 1,704,564 A | 3/1929 | Friedland |
| 1,753,290 A | 4/1930 | Graves |
| 1,758,632 A | 5/1930 | Wagner |
| 1,764,130 A | 6/1930 | Vardeman |
| 1,796,893 A | 3/1931 | McVeigh |
| 1,797,946 A | 3/1931 | Eichel |
| 1,863,389 A | 5/1931 | Anderson |
| 1,840,246 A | 1/1932 | Newman |
| 1,908,510 A | 5/1933 | Dodson |
| 1,963,389 A | 6/1934 | Vardeman |
| 1,993,662 A | 3/1935 | Green |
| 2,042,239 A | 5/1936 | Planding |
| 2,155,473 A | 9/1936 | Coleman |
| 2,088,839 A | 8/1937 | Coney et al. |
| 2,117,174 A | 5/1938 | Jones |
| 2,129,082 A | 9/1938 | Byrer |
| 2,139,245 A | 12/1938 | Ogden |
| 2,154,846 A | 4/1939 | Heymann et al. |
| 2,164,219 A | 6/1939 | McGerry |
| 2,172,624 A | 9/1939 | Gabriel et al. |
| 2,176,309 A | 10/1939 | Love et al. |
| 2,189,175 A | 2/1940 | Jackson |
| 2,206,726 A | 7/1940 | Lasater |
| 2,219,753 A | 10/1940 | Seguin |
| 2,225,331 A | 12/1940 | Campbell |
| 2,238,603 A | 4/1941 | Runnels |
| 2,244,699 A | 6/1941 | Hosey |
| 2,246,867 A | 6/1941 | Thomas et al. |
| 2,263,802 A | 11/1941 | Grusin |
| 2,266,195 A | 12/1941 | Lay |
| 2,279,355 A | 4/1942 | Wilensky |
| 2,312,828 A | 3/1943 | Adamsson |
| 2,326,632 A | 8/1943 | Friedman |
| 2,328,998 A | 9/1943 | Radford |
| 2,364,205 A | 12/1944 | Fuller |
| 2,486,203 A | 10/1949 | Pieper |
| 2,486,847 A | 11/1949 | Hokett |
| 2,556,691 A | 6/1951 | Harshbarger |
| 2,604,649 A | 7/1952 | Stephenson et al. |
| 2,637,870 A | 5/1953 | Cohen |
| 2,702,914 A | 3/1955 | Kittle et al. |
| 2,832,088 A | 4/1958 | Peilet et al. |
| 2,882,544 A | 4/1959 | Hadidian |
| 2,935,755 A | 5/1960 | Leira et al. |
| 3,007,441 A | 11/1961 | Eyer |
| 3,016,554 A | 1/1962 | Peterson |
| 3,050,072 A | 8/1962 | Diener |
| 3,103,027 A | 9/1963 | Birch |
| 3,110,918 A | 11/1963 | Tate, Jr. |
| 3,128,487 A | 4/1964 | Vallis |
| 3,129,449 A | 4/1964 | Cyzer |
| 3,159,859 A | 12/1964 | Rasmussen |
| 3,177,509 A | 4/1965 | Cyzer |
| 3,230,562 A | 1/1966 | Birch |
| 3,258,805 A | 7/1966 | Rossnan |
| 3,295,156 A | 1/1967 | Brant |
| 3,302,230 A | 2/1967 | Poppelman |
| 3,316,576 A | 5/1967 | Urbrush |
| 3,327,339 A | 6/1967 | Lemelson |
| 3,359,588 A | 12/1967 | Kobler |
| 3,398,421 A | 8/1968 | Rashbaum |
| 3,403,070 A | 9/1968 | Lewis, Jr. |
| 3,411,979 A | 11/1968 | Lewis |
| RE26,688 E | 10/1969 | Lemelson |
| 3,553,759 A | 1/1971 | Kramer et al. |
| 3,613,143 A | 10/1971 | Muhler et al. |
| 4,033,008 A | 7/1977 | Warren et al. |
| 4,081,877 A | 4/1978 | Vitale |
| 4,114,222 A | 9/1978 | Serediuk |
| 4,128,910 A | 12/1978 | Nakata et al. |
| 4,156,620 A | 5/1979 | Clemens |
| 4,202,361 A | 5/1980 | Bills |
| 4,263,691 A | 4/1981 | Pakarnseree |
| 4,277,862 A | 7/1981 | Weideman |
| 4,288,883 A | 9/1981 | Dolinsky |
| 4,356,585 A | 11/1982 | Protell et al. |
| 4,373,541 A | 2/1983 | Nishioka |
| 4,391,951 A | 7/1983 | Scheetz |
| 4,403,623 A | 9/1983 | Mark |
| 4,409,701 A | 10/1983 | Perches |
| 4,429,434 A | 2/1984 | Sung-Shan |
| 4,472,853 A | 9/1984 | Rauch |
| 4,476,280 A | 10/1984 | Poppe et al. |
| 4,480,351 A | 11/1984 | Koffler |
| 4,517,701 A | 5/1985 | Stanford, Jr. |
| 4,525,531 A | 6/1985 | Zukosky et al. |
| 4,534,081 A | 8/1985 | Spademan |
| 4,545,087 A | 10/1985 | Nahum |
| 4,585,416 A | 4/1986 | DeNiro et al. |
| 4,603,166 A | 7/1986 | Poppe et al. |
| 4,616,064 A | 10/1986 | Zukosky et al. |
| 4,617,342 A | 10/1986 | Poppe et al. |
| 4,617,694 A | 10/1986 | Bori |
| 4,623,495 A | 11/1986 | Degoix et al. |
| 4,633,542 A | 1/1987 | Taravel |
| 4,654,922 A | 4/1987 | Chen |
| 4,672,706 A | 6/1987 | Hill |
| 4,691,405 A | 9/1987 | Reed |
| 4,694,844 A | 9/1987 | Berl et al. |
| 4,706,322 A | 11/1987 | Nicolas |
| 4,751,761 A | 6/1988 | Breitschmid |
| 4,776,054 A | 10/1988 | Rauch |
| 4,783,874 A | 11/1988 | Perches et al. |
| 4,802,255 A | 2/1989 | Breuer et al. |
| 4,833,194 A | 5/1989 | Kuan et al. |
| 4,845,795 A | 7/1989 | Crawford et al. |
| 4,852,202 A | 8/1989 | Ledwitz |
| 4,882,803 A | 11/1989 | Rogers et al. |
| 4,892,698 A | 1/1990 | Weihrauch |
| 4,894,880 A | 1/1990 | Aznavoorian |
| 4,913,133 A | 4/1990 | Tichy |
| 4,979,782 A | 12/1990 | Weihrauch |
| 4,989,287 A | 2/1991 | Scherer |
| 4,991,249 A | 2/1991 | Suroff |
| 5,020,179 A | 6/1991 | Scherer |
| 5,021,475 A | 6/1991 | Isayev |
| 5,034,450 A | 7/1991 | Betz et al. |
| 5,040,260 A | 8/1991 | Michaels |
| D325,821 S | 5/1992 | Schwartz |
| 5,114,214 A | 5/1992 | Barman |
| 5,120,225 A | 6/1992 | Amit |
| 5,137,039 A | 8/1992 | Klinkhammer |
| 5,142,724 A | 9/1992 | Park |
| 5,165,131 A | 11/1992 | Staar |
| 5,184,368 A | 2/1993 | Holland |
| 5,186,627 A | 2/1993 | Amit et al. |
| 5,228,166 A | 7/1993 | Gomez |

(56) References Cited

U.S. PATENT DOCUMENTS

| | | |
|---|---|---|
| 5,269,038 A | 12/1993 | Bradley |
| D345,054 S | 3/1994 | Spence, Jr. |
| 5,291,878 A | 3/1994 | Lombardo et al. |
| 5,313,909 A | 5/1994 | Tseng et al. |
| 5,318,352 A | 6/1994 | Holland |
| 5,321,726 A | 6/1994 | Kafadar |
| 5,325,560 A | 7/1994 | Pavone et al. |
| 5,334,646 A | 8/1994 | Chen |
| D350,851 S | 9/1994 | Spence, Jr. |
| 5,350,248 A | 9/1994 | Chen |
| 5,357,644 A | 10/1994 | Theriault |
| 5,392,483 A | 2/1995 | Heinzelman et al. |
| 5,398,366 A | 3/1995 | Bradley |
| 5,407,254 A | 4/1995 | Hegemann |
| 5,421,726 A | 6/1995 | Okada |
| 5,435,032 A | 7/1995 | McDougall |
| 5,458,400 A | 10/1995 | Meyer |
| 5,476,384 A | 12/1995 | Giuliani et al. |
| 5,524,319 A | 6/1996 | Avidor |
| 5,528,786 A | 6/1996 | Porat et al. |
| 5,535,474 A | 7/1996 | Salazar |
| 5,546,626 A | 8/1996 | Chung |
| 5,590,434 A | 1/1997 | Imai |
| 5,593,213 A | 1/1997 | Meessmann |
| 5,604,951 A | 2/1997 | Shipp |
| 5,628,082 A | 5/1997 | Moskovich |
| 5,651,157 A | 7/1997 | Hahn |
| 5,678,275 A | 10/1997 | Derfner |
| D386,617 S | 11/1997 | Shyu |
| 5,706,542 A | 1/1998 | Okaka |
| 5,722,106 A | 3/1998 | Masterman et al. |
| 5,723,543 A | 3/1998 | Modic |
| 5,735,011 A | 4/1998 | Asher |
| 5,742,972 A * | 4/1998 | Bredall et al. ............... 15/167.1 |
| 5,778,474 A | 7/1998 | Shek |
| 5,791,007 A | 8/1998 | Tsai |
| 5,799,354 A | 9/1998 | Amir |
| 5,802,656 A | 9/1998 | Dawson et al. |
| 5,813,079 A | 9/1998 | Halm |
| 5,823,633 A | 10/1998 | Weihrauch |
| D401,414 S | 11/1998 | Vrignaud |
| 5,836,033 A | 11/1998 | Berge |
| 5,839,148 A | 11/1998 | Volpenhein |
| 5,842,249 A | 12/1998 | Sato |
| 5,864,915 A | 2/1999 | Ra |
| 5,896,614 A | 4/1999 | Flewitt |
| 5,930,860 A | 8/1999 | Shipp |
| 5,946,759 A | 9/1999 | Cann |
| 5,970,564 A | 10/1999 | Inns et al. |
| 5,974,619 A | 11/1999 | Weihrauch |
| 5,987,681 A | 11/1999 | Hahn et al. |
| 5,987,688 A | 11/1999 | Roberts et al. |
| 5,991,959 A | 11/1999 | Raven et al. |
| 6,018,840 A | 2/2000 | Guay et al. |
| 6,035,476 A | 3/2000 | Underwood et al. |
| 6,041,467 A * | 3/2000 | Roberts et al. ............... 15/167.1 |
| 6,058,541 A | 5/2000 | Masterman et al. |
| 6,067,684 A | 5/2000 | Kweon |
| 6,088,870 A | 7/2000 | Hohlbein |
| 6,112,361 A | 9/2000 | Brice |
| 6,138,310 A | 10/2000 | Porper et al. |
| 6,151,745 A | 11/2000 | Roberts et al. |
| 6,161,245 A | 12/2000 | Weihrauch |
| 6,178,582 B1 | 1/2001 | Halm |
| 6,199,242 B1 | 3/2001 | Masterman et al. |
| 6,202,241 B1 | 3/2001 | Hassell et al. |
| D440,048 S | 4/2001 | Beals et al. |
| 6,209,164 B1 | 4/2001 | Sato |
| D443,985 S | 6/2001 | Beals et al. |
| 6,253,404 B1 | 7/2001 | Boland et al. |
| 6,286,173 B1 | 9/2001 | Briones |
| 6,290,302 B1 | 9/2001 | Boucherie |
| 6,290,303 B1 | 9/2001 | Boucherie |
| 6,298,516 B1 | 10/2001 | Beals et al. |
| 6,308,367 B1 | 10/2001 | Beals et al. |
| 6,363,565 B1 | 4/2002 | Paffrath |
| 6,389,634 B1 | 5/2002 | Devlin et al. |
| 6,391,445 B1 | 5/2002 | Weihrauch |
| 6,405,401 B1 | 6/2002 | Hellerud et al. |
| 6,421,865 B1 | 7/2002 | McDougall |
| 6,421,867 B1 | 7/2002 | Weihrauch |
| 6,453,497 B1 | 9/2002 | Chiang et al. |
| 6,463,618 B1 | 10/2002 | Zimmer |
| 6,477,729 B1 | 11/2002 | Ben-Ari |
| 6,513,182 B1 | 2/2003 | Calabrese et al. |
| 6,553,604 B1 | 4/2003 | Braun et al. |
| 6,564,416 B1 | 5/2003 | Claire et al. |
| 6,571,417 B1 | 6/2003 | Gavney, Jr. et al. |
| 6,658,688 B2 | 12/2003 | Gavney, Jr. |
| 6,701,565 B2 | 3/2004 | Hafemann |
| 6,725,490 B2 | 4/2004 | Blaustein et al. |
| 6,776,597 B2 | 8/2004 | Buhler |
| 6,807,703 B2 | 10/2004 | Van Gelder et al. |
| 6,820,300 B2 | 11/2004 | Gavney, Jr. |
| 6,826,797 B1 | 12/2004 | Chenvainu et al. |
| 6,859,969 B2 | 3/2005 | Gavney, Jr. et al. |
| 6,889,401 B2 | 5/2005 | Fattori et al. |
| 6,892,412 B2 | 5/2005 | Gatzemeyer et al. |
| 6,892,413 B2 | 5/2005 | Blaustein et al. |
| 6,918,154 B2 | 7/2005 | Ben-Ari |
| 6,931,688 B2 | 8/2005 | Moskovich et al. |
| 6,938,294 B2 | 9/2005 | Fattor et al. |
| 6,988,777 B2 | 1/2006 | Pfenniger et al. |
| 6,993,804 B1 | 2/2006 | Braun et al. |
| 7,008,225 B2 | 3/2006 | Ito et al. |
| 7,160,508 B2 | 1/2007 | Lee |
| 7,222,381 B2 | 5/2007 | Kraemer |
| 7,225,494 B2 | 6/2007 | Chan et al. |
| 7,251,849 B2 | 8/2007 | Moskovich et al. |
| 7,392,562 B2 | 7/2008 | Boland et al. |
| 2001/0007161 A1 | 7/2001 | Masterman et al. |
| 2001/0013151 A1 | 8/2001 | Gelder et al. |
| 2001/0020314 A1 | 9/2001 | Calabrese |
| 2002/0004964 A1 | 1/2002 | Luchino et al. |
| 2002/0084550 A1 | 7/2002 | Roberts et al. |
| 2002/0192621 A1 | 12/2002 | Ben-Ari |
| 2003/0033680 A1 | 2/2003 | Davies et al. |
| 2003/0033682 A1 | 2/2003 | Davies et al. |
| 2003/0041402 A1 | 3/2003 | Stein |
| 2003/0066147 A1 | 4/2003 | Roh |
| 2003/0077107 A1 | 4/2003 | Kuo |
| 2003/0079304 A1 | 5/2003 | Dworzan |
| 2003/0084525 A1 | 5/2003 | Blaustein |
| 2003/0140440 A1 | 7/2003 | Gavney, Jr. |
| 2003/0159224 A1 | 8/2003 | Fischer et al. |
| 2003/0196283 A1 | 10/2003 | Eliav et al. |
| 2003/0229959 A1 | 12/2003 | Gavney, Jr. et al. |
| 2004/0010869 A1 | 1/2004 | Fattori et al. |
| 2004/0025275 A1 | 2/2004 | Moskovich et al. |
| 2004/0060132 A1 | 4/2004 | Gatzemeyer et al. |
| 2004/0060133 A1 | 4/2004 | Eliav |
| 2004/0060137 A1 | 4/2004 | Eliav |
| 2004/0068809 A1 | 4/2004 | Weng |
| 2004/0083566 A1 | 5/2004 | Blaustein et al. |
| 2004/0084063 A1 | 5/2004 | Vago et al. |
| 2004/0123409 A1 | 7/2004 | Dickie |
| 2004/0128784 A1 | 7/2004 | Ben-Ari |
| 2004/0168271 A1 | 9/2004 | McDougall |
| 2004/0177458 A1 | 9/2004 | Chan et al. |
| 2004/0177462 A1 | 9/2004 | Duff et al. |
| 2004/0221409 A1 | 11/2004 | Gavney, Jr. |
| 2004/0231076 A1 | 11/2004 | Gavney, Jr. |
| 2004/0231082 A1 | 11/2004 | Gavney, Jr. |
| 2004/0237236 A1 | 12/2004 | Gavney, Jr. |
| 2004/0261203 A1 | 12/2004 | Dworzan |
| 2005/0015901 A1 | 1/2005 | Gavney, Jr. |
| 2005/0060822 A1 | 3/2005 | Chenvainu et al. |
| 2005/0235439 A1 | 10/2005 | Braun et al. |
| 2005/0273961 A1 | 12/2005 | Moskovich et al. |
| 2006/0272112 A9 | 12/2006 | Braun et al. |
| 2008/0060155 A1 | 3/2008 | Braun et al. |

(56) References Cited

U.S. PATENT DOCUMENTS

| | | | |
|---|---|---|---|
| 2009/0172900 A1 | 7/2009 | Brown, Jr. et al. | |
| 2010/0162499 A1 | 7/2010 | Braun et al. | |

FOREIGN PATENT DOCUMENTS

| | | |
|---|---|---|
| CA | 2483825 | 10/2005 |
| CH | 103 194 | 1/1924 |
| CH | 169312 | 5/1934 |
| CH | 609238 | 2/1979 |
| CN | 2119280 U | 10/1992 |
| DE | 558 852 | 9/1932 |
| DE | 813 990 | 5/1952 |
| DE | 1 883 020 | 11/1963 |
| DE | 1210409 | 2/1966 |
| DE | 7343826 U | 11/1974 |
| DE | 2 402 785 | 7/1975 |
| DE | 75 33 143 U | 2/1976 |
| DE | 2500132 A1 | 7/1976 |
| DE | 25 46 712 A1 | 4/1977 |
| DE | 2715414 A1 | 10/1978 |
| DE | 82 15 266.7 U1 | 9/1982 |
| DE | 35 29 953 A1 | 3/1987 |
| DE | 37 44 630 A1 | 7/1989 |
| DE | 3928919 | 3/1991 |
| DE | 42 07 968 | 9/1993 |
| DE | 94 00 231.2 U1 | 3/1994 |
| DE | 4412301 | 10/1995 |
| DE | 19817704 | 10/1999 |
| DE | 29919053 | 12/2000 |
| DE | 100 28 530 A1 | 12/2001 |
| DK | 0076598 | 11/1953 |
| EP | 0 189 816 A2 | 8/1986 |
| EP | 0322562 | 7/1989 |
| EP | 0 360 766 A1 | 3/1990 |
| EP | 0 704 179 A1 | 4/1996 |
| EP | 0 783 850 B1 | 3/2001 |
| EP | 1 080 664 | 3/2001 |
| EP | 0 870 440 B1 | 12/2001 |
| EP | 1 449 496 B1 | 9/2008 |
| FR | 459442 | 11/1913 |
| FR | 936529 | 6/1948 |
| FR | 1075171 | 10/1954 |
| FR | 2541100 | 8/1984 |
| FR | 2548528 | 1/1985 |
| FR | 2559361 | 8/1985 |
| FR | 2 612 751 | 9/1988 |
| FR | 2 616 306 | 12/1988 |
| FR | 2 789 887 | 8/2000 |
| GB | 193 601 A | 3/1923 |
| GB | 280 067 A | 11/1927 |
| GB | 378 129 A | 8/1932 |
| GB | 490 892 A | 8/1938 |
| GB | 690 422 A | 4/1953 |
| GB | 1 164 597 A | 9/1969 |
| GB | 1 325 860 A | 8/1973 |
| GB | 1 537 526 | 12/1978 |
| GB | 2137080 | 10/1984 |
| GB | 2 214 420 A | 9/1989 |
| GB | 2247297 | 2/1992 |
| GB | 2 354 432 A | 3/2001 |
| JP | 50-11769 | 2/1975 |
| JP | 51-056165 U | 5/1976 |
| JP | 52-125962 U | 9/1977 |
| JP | 58-091931 U | 6/1983 |
| JP | 61-187531 U | 11/1986 |
| JP | 63-066928 U | 5/1988 |
| JP | 1-72128 | 5/1989 |
| JP | 2-119031 | 7/1990 |
| JP | 2-180203 | 7/1990 |
| JP | 3-3226 | 1/1991 |
| JP | 3-312978 | 9/1991 |
| JP | 4-128627 | 11/1992 |
| JP | 5-69342 | 3/1993 |
| JP | 05-76416 | 3/1993 |
| JP | 05096597 | 4/1993 |
| JP | 5-123222 | 5/1993 |
| JP | 6-327517 A2 | 11/1994 |
| JP | 08103326 | 4/1996 |
| JP | 08103332 | 4/1996 |
| JP | 61-90877 | 5/1996 |
| JP | 08257043 | 8/1996 |
| JP | 08299372 | 11/1996 |
| JP | 9-140456 | 3/1997 |
| JP | 9-187319 A2 | 7/1997 |
| JP | 2000-157338 | 6/2000 |
| JP | 2000-300345 | 10/2000 |
| JP | 2000-300347 | 10/2000 |
| JP | 2000-308524 | 11/2000 |
| JP | 2001-190333 | 7/2001 |
| JP | 2001-507360 | 7/2001 |
| JP | 2002-010832 | 1/2002 |
| JP | 2002-248118 | 9/2002 |
| JP | 200361986 | 3/2003 |
| JP | 2003093415 | 4/2003 |
| JP | 2003164473 | 6/2003 |
| RU | 2045216 | 10/1995 |
| SU | 1687243 | 10/1991 |
| SU | 1752336 | 8/1992 |
| WO | WO 91/05088 | 4/1991 |
| WO | WO 92/04589 | 3/1992 |
| WO | WO 93/24034 | 12/1993 |
| WO | WO 95/01113 A1 | 1/1995 |
| WO | WO 96/15696 | 5/1996 |
| WO | WO 97/14330 | 4/1997 |
| WO | WO 98/01055 | 1/1998 |
| WO | WO 98/18364 | 5/1998 |
| WO | WO 99/37181 | 7/1999 |
| WO | WO 00/21406 | 4/2000 |
| WO | WO 00/30495 | 6/2000 |
| WO | WO 00/34022 | 6/2000 |
| WO | WO 00/47083 | 8/2000 |
| WO | WO 00/64307 | 11/2000 |
| WO | WO 00/76369 A2 | 12/2000 |
| WO | WO 01/21036 A1 | 3/2001 |
| WO | WO 01/43586 | 6/2001 |
| WO | WO 01/87101 A2 | 11/2001 |
| WO | WO 01/89344 | 11/2001 |
| WO | WO 02/05679 A1 | 1/2002 |
| WO | WO 02/11583 | 2/2002 |
| WO | WO 02/19942 A1 | 3/2002 |
| WO | WO 02/38004 | 5/2002 |
| WO | WO 02/45617 | 6/2002 |
| WO | WO 03/086140 A1 | 10/2003 |
| WO | WO 2004/014181 A1 | 2/2004 |

OTHER PUBLICATIONS

"Santroprene Rubber Physical Properties Guide, Tensile Properties, Dynamic Mechanical Properties, Tension and Compression Set, Fatigue Resistance", Advanced Elastomer Systems, pp. 2-19, Undated.
"Distinctive Plastics—Multi-Component Molding" http://www.distinctiveplastics.com/html/?id=2 copyright 2006.
"Plastics—Determination of flexural properties", British Standard, BS EN ISO 178:2003, Apr. 9, 2003.
Plastics Extrusion Technology Handbook Chapter Seven, Coextrusion and Dual-Extrusion Technology, pp. 168-189.
Modern Plastic Encyclopedia, 67:168-175, 1990.
Pebax 3533 SA 00, "Base Polymer for Structural Hot Melt Adhesives".
Product Literature, Kraton Polymers, pp. 13-21.
"Standard Test Methods for Flexural Properties of Unreinforced and Reinforced Plastics and Electrical Insulating Materials [Metric]", American Society for Testing Materials, Designation: D790M-93 Metric, pp. 1-9, Undated.
"Standard Terminology Relating to Plastics", American Society for Testing Materials, Designation: D883-00, pp. 1-15, Undated.
Hendricks et al., "Rubber-Related Polymers I. Thermoplastic Elastomers", Rubber Technology, pp. 515-533, Undated.
Office Action for U.S. Appl. No. 10/389,448 dated Feb. 25, 2009; Braun et al.; filing date Mar. 14, 2003.

(56) References Cited

OTHER PUBLICATIONS

Office Action for U.S. Appl. No. 10/389,448 dated Feb. 22, 2007; Braun et al.; filing date Mar. 14, 2003.
Office Action for U.S. Appl. No. 12/186,639 dated Dec. 23, 2009; Braun et al.; filing date Aug. 6, 2008.
Office Action for U.S. Appl. No. 10/830,693 dated Feb. 26, 2009; Masterman et al.; filing date Apr. 23, 2004.
Office Action for U.S. Appl. No. 10/830,693 dated Jul. 2, 2008; Masterman et al.; filing date Apr. 23, 2004.
Office Action for U.S. Appl. No. 10/830,693 dated Mar. 3, 2008; Masterman et al.; filing date Apr. 23, 2004.
Office Action for U.S. Appl. No. 10/830,693 dated Oct. 24, 2007; Masterman et al.; filing date Apr. 23, 2004.
Office Action for U.S. Appl. No. 10/830,693 dated May 15, 2007; Masterman et al.; filing date Apr. 23, 2004.
Office Action for U.S. Appl. No. 10/830,693 dated Aug. 17, 2006; Masterman et al.; filing date Apr. 23, 2004.
Office Action for U.S. Appl. No. 10/799,793 dated Jun. 19, 2009; Braun et al.; filing date May 2, 2007.
Office Action for U.S. Appl. No. 10/799,793 dated Apr. 25, 2008; Braun et al.; filing date May 2, 2007.
Office Action for U.S. Appl. No. 10/820,562 dated Jun. 4, 2010; Braun et al.; filing date Mar. 16, 2000.
Office Action for U.S. Appl. No. 10/820,562 dated Jul. 27, 2009; Braun et al.; filing date Mar. 16, 2000.
Office Action for U.S. Appl. No. 10/820,562 dated Jul. 5, 2007; Braun et al.; filing date Mar. 16, 2000.
Office Action for U.S. Appl. No. 10/820,562 dated May 8, 2006; Braun et al.; filing date Mar. 16, 2000.
Office Action for U.S. Appl. No. 10/820,562 dated Aug. 15, 2005; Braun et al.; filing date Mar. 16, 2000.

* cited by examiner

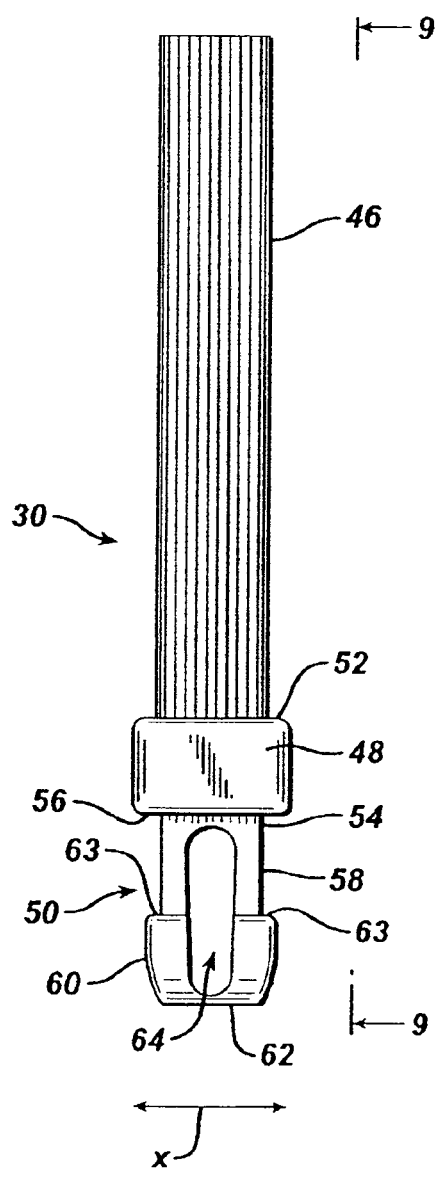
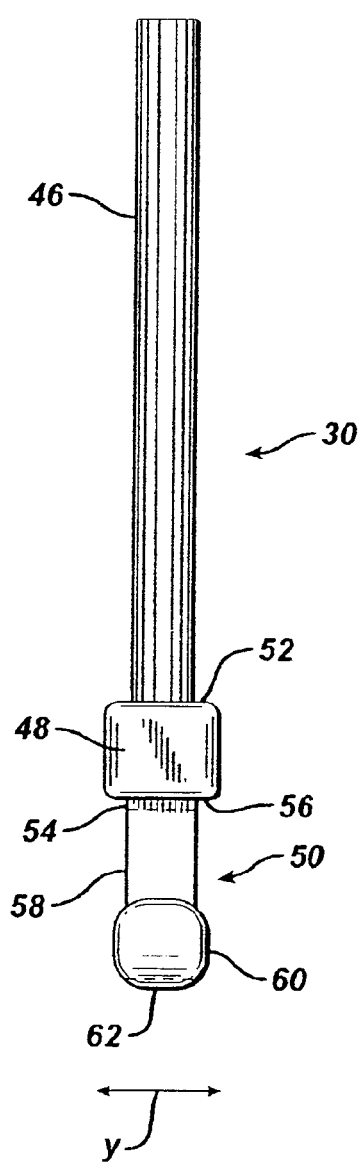

TOOTHBRUSH HEAD

FIELD OF THE INVENTION

The invention relates generally to the field of oral care, and in particular to toothbrushes. More specifically, the invention relates to a toothbrush head having one or more pivoting tufts of bristles, the head having two portions that can move independent of each other.

BACKGROUND OF THE INVENTION

A Japanese patent document having an application number of 3-312978 discloses a toothbrush having a multiplicity of tufts of nylon bristles. In a first embodiment shown in FIGS. 1, 2 and 3 of the document, a plurality of cylindrical recessed sections in the head are set orthogonally to the longitudinal axial direction of a shank and are formed at equal intervals. Column-shaped rotary bodies 5 are respectively contained in the recessed sections. On the peripheral surfaces of the rotary bodies 5, along the axial direction, projected strip sections 5a are formed, and they are set in a state that they are positioned at the opening sections of the recessed sections. At the opening sections of the recessed sections, contact surfaces to be positioned on both the sides are formed. At both the ends of the upper surfaces of the projected strip sections 5a, nylon bristles 6 are arranged to be vertically erected.

As shown in FIG. 3 of the document, the arrangement described above allows bristles 6 to rotate during use of the brush. A problem with this brush is that two tufts of bristles are secured to each strip section 5a and thus must rotate in unison. As a result, an individual tuft of bristles cannot rotate independently of its "partner" tuft. The individual tuft may thus be prevented from achieving optimal penetration between two teeth during brushing because the partner tuft might contact the teeth in a different manner and interfere with rotation of the individual tuft.

FIGS. 4, 5 and 6 of the document disclose a second embodiment in which each tuft of bristles is secured to the head by a ball and socket type arrangement. While this embodiment allows each tuft of bristles to swivel independent of the other tufts, it does have disadvantages. If a tuft of bristles is tilted out towards the side of the head and that tuft is positioned near the interface between the side and top surfaces of the teeth, chances are increased that the bristle tips will not even be in contact with the teeth during brushing. Further, the random orientation in which the tufts can end up after brushing detracts from the attractiveness of the brush.

The Japanese reference also discloses that the brush head is made of a unitary structure. As such, water cannot flow through any central portion of the brush head, thereby inhibiting the cleanability of the brush. Further, the unitary head structure does not allow different portions of the head to move independently of each other. Accordingly, the bristle tufts extending from the tuft cannot accommodate the varying tooth surfaces as well as a brush in which the head has two or more portions that can move or flex independent of each other.

SUMMARY OF THE INVENTION

The present invention is directed to overcoming one or more of the problems set forth above.

In one embodiment, a toothbrush head comprises a top surface and a bottom surface opposite the top surface. The head further comprises a first portion, a second portion, and an opening between the first portion and the second portion. The opening extends from the top surface to the bottom surface. A first plurality of contact elements are positioned on the first portion and the second portion, and a second plurality of contact elements are positioned on the first portion and the second portion. Each of the second plurality of contact elements comprises an elastomer.

These and other aspects, objects, features and advantages of the present invention will be more clearly understood and appreciated from a review of the following detailed description of the preferred embodiments and appended claims, and by reference to the accompanying drawings.

BRIEF DESCRIPTION OF THE DRAWINGS

FIG. 8 is a front view of a pivoting tuft taken along the lines 8-8 of FIG. 13;

FIG. 9 is a side view of the pivoting tuft of FIG. 8 taken along lines 9-9;

DETAILED DESCRIPTION

Figure 5:
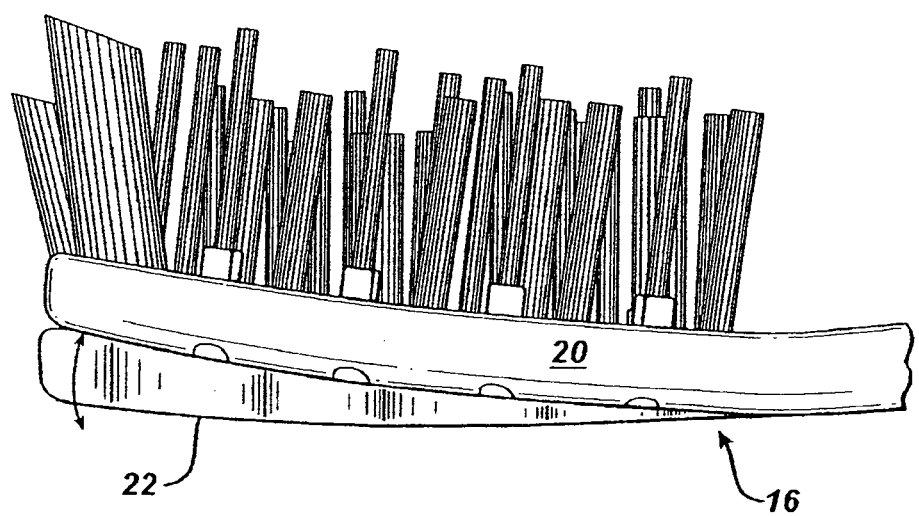
FIG. 5 is a side view of the head of FIG. 1 showing one of the head portions flexing.

Beginning with FIGS. 1-5, there is shown a toothbrush head 16 which extends from a neck 14 which extends from a handle (not shown) to form a toothbrush. The type of handle is not germane to the present invention. The head and handle are preferably made of polypropylene. The head has a serpentine split 18 which divides the head into two portions 20 and 22. An end of the split 13 near neck 14 is preferably circular in shape (see FIG. 2). As shown in FIG. 5, the split in the head allows portions 20 and 22 to flex or move independent of each other during use of the toothbrush, thus facilitating cleaning of the teeth.

Split 18 can also be defined as an opening in the head between head portions 20 and 22. This opening allows water to flow through the head, thereby enhancing cleaning of the top head surface which typically gets caked with toothpaste in spite of efforts to rinse the head clean.

Head portion 20 includes a projecting part 24 which fits (at least partially) into a recess 26 (see FIG. 6) defined by portion 22. Projecting part 24 has several tufts of bristles extending from it (to be described in further detail below) and is surrounded on three sides by head portion 22.

Figure 1:
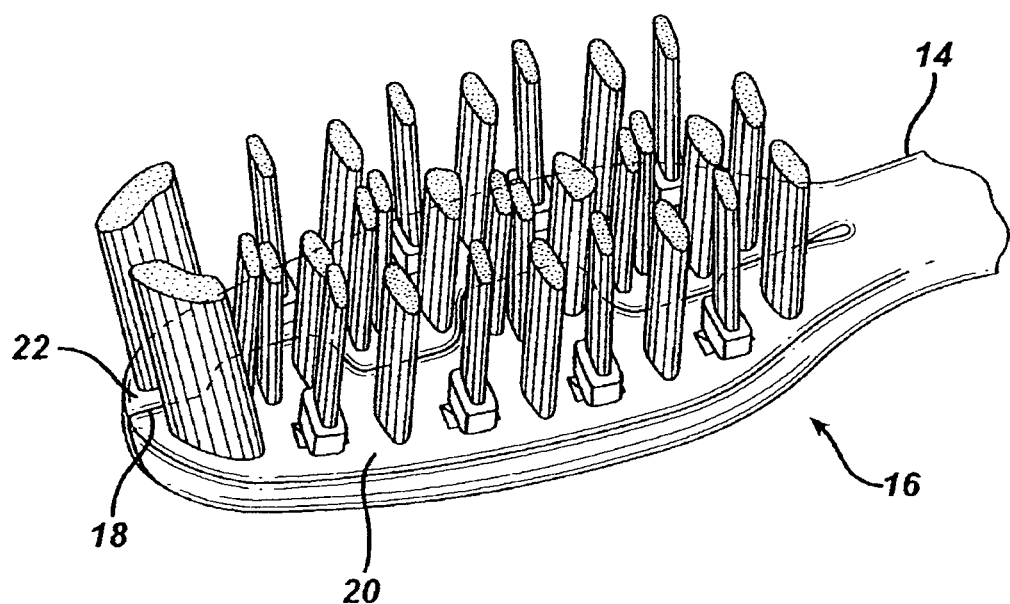
FIG. 1 is a perspective view of the toothbrush head of FIG. 1.
Figure 2:
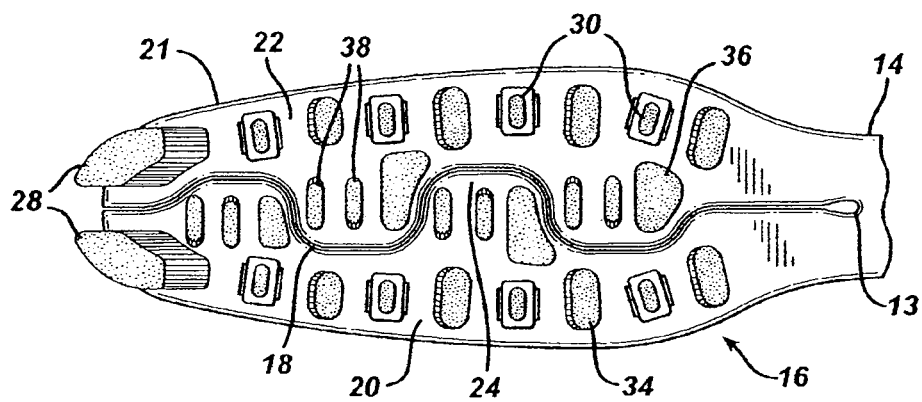
FIG. 2 is a top view of the head of FIG. 1.
Figure 3:
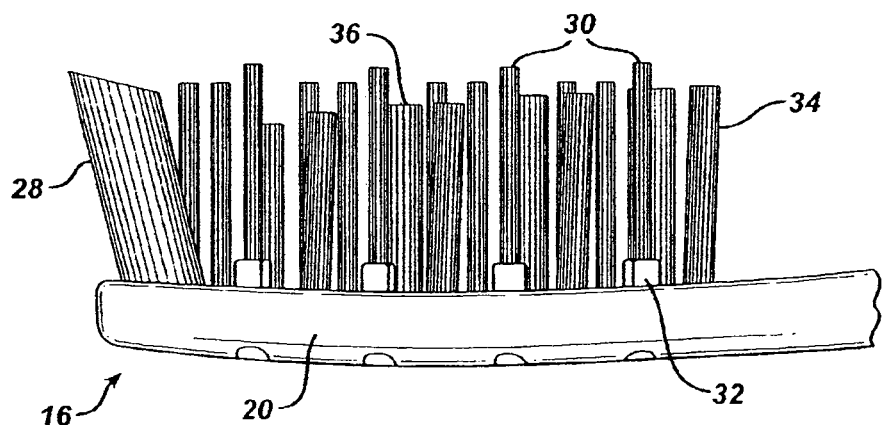
FIG. 3 is a side view of the head of FIG. 1.
Figure 4:
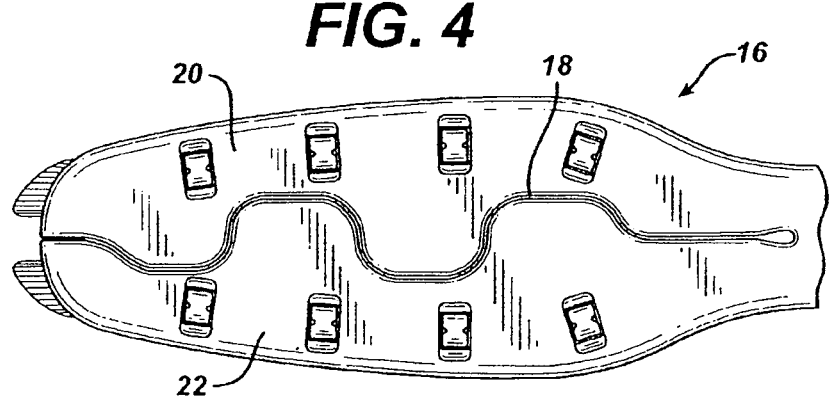
FIG. 4 is a bottom view of the head of FIG. 1.

Referring now to FIGS. 2 and 3, each of the tufts of bristles on head 16 will be described. A first pair of tufts 28 are located towards the free end of the head, one on each head portion 20, 22. Each tuft has bristles (tooth cleaners) which preferably are each made of polybutylene-terepthalate (PBT) and have a diameter of 0.007 inches. The shortest bristles in tuft 28 have a length of 0.420 inches with the remaining bristles increasing in length steadily to a tip of the tuft. Each tuft tilts away from the handle by an angle of preferably about 12 degrees relative to that portion of the surface of the head from which it projects. As shown in FIG. 2, tufts 28 have a larger cross-section than any other tuft on the head.

A second group of tufts are pivoting tufts 30 (the only tufts on the head which are rotatable). There are four tufts 30 on each head portion 20, 22 which are located towards the outside of the head. Each tuft 30 can pivot up to about 15 degrees to either side of a vertical position on the head, more preferably being able to pivot up to about 8 degrees to either side of a vertical position on the head. The pivoting of tufts 30 is roughly towards or away from neck 14. Each tuft 30 includes a base support 32 made of polypropylene. The bristles are made of polyamid 6.12, have a diameter of 0.008 inches and extend 0.420 inches above the base support.

A third group of tufts 34 extend perpendicular to the head. There are four tufts 34 on each head portion 20, 22 which alternate with tufts 30. When viewed from the top (FIG. 2) the tufts are oval in shape (similar to tufts 30 but larger). In other words, the tufts 34 and 30 have oval shaped cross-sections. Each tuft 34 has bristles which are made of polyamid 6.12, have a diameter of 0.006 inches and extend above the head by about 0.385 inches.

A fourth group of tufts 36 are located towards the inside of the head. There are two such tufts on each head portion 20, 22. Each tuft 36 extends perpendicular to the head. The bristles of tuft 36 have a diameter of 0.006 inches, are made of polyamid 6.12 and rise about 0.360 inches above the head.

A fifth and final group of tufts 38 are also located towards the inside of the head (away from a perimeter 21 of the head). There are 4 pairs of tufts 38. In each pair one tuft is closer to neck 14 than the other tuft. In each pair of tufts 38, (a) a base of one tuft is closer to a first side of the head and this one tuft leans towards a second side of the head, and (b) a base of the other tuft is closer to the second side of the head and this other tuft leans towards the first side of the head. As such, the tufts in each pair lean across each other. The angle of tilt towards the side of the head is about five degrees. Each tuft 38 bristles which are made of PBT, have a bristle diameter of about 0.007 inches and extend about 0.460 inches above head 16. Each tuft 38 has an oval cross-section with a long dimension of the oval being oriented in the direction of tilt.

The bristles used on the head can be crimped (see U.S. Pat. No. 6,058,541) or notched (see U.S. Pat. No. 6,018,840). Other types of tooth cleaners besides bristles can be used. For example, a tuft of bristles could be replaced by an elastomeric fin. The US patents listed in this paragraph are incorporated herein by reference.

Figure 6:
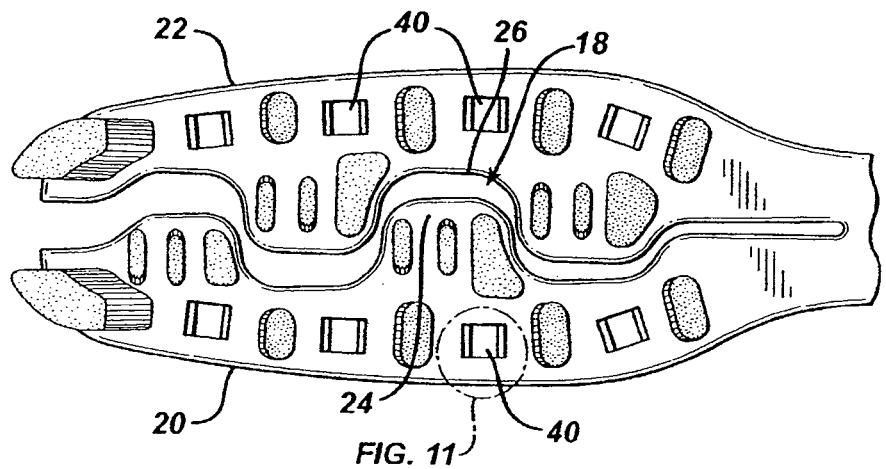
FIG. 6 is a top view of the head of FIG. 1 with the two head portions separated from each other.

Turning now to FIG. 6, a description will now be provided as to how the toothbrush (head) is made. In a first step, the head, neck and handle of the toothbrush are injection molded in a mold. During this injection molding step, tufts 28, 34, 36 and 38 are secured in the head by a hot-tufting process. Hot-tufting processes are notoriously well known by those skilled in the art (see e.g. U.S. Pat. No. 4,635,313; and 6,361, 120; British patent application 2,330,791; and European patent application 676,268 A1).

Briefly, hot-tufting involves presenting ends of a multiplicity of groups of plastic filaments into a mold. Each group of filament ends inside the mold is optionally melted into a blob. Each filament group is cut to a desired length (either before or after being introduced into the mold) to form a tuft of bristles. The mold is closed and molten plastic is injected into the mold. When the plastic solidifies, it locks one end of the tufts of bristles into the head of the toothbrush.

It can be seen in FIG. 6 that the opening 18 between head portions 20 and 22 is much wider at this point than in the heads final form (see FIG. 2). In other words, head portions 20 and 22 are spaced a predetermined distance (preferably at least about 1 mm) from each other. Further, through holes 40 are created during the molding step for receiving pivoting tufts 30 at a later point in the manufacturing process. Holes 40 will be described in greater detail below.

Figure 7:
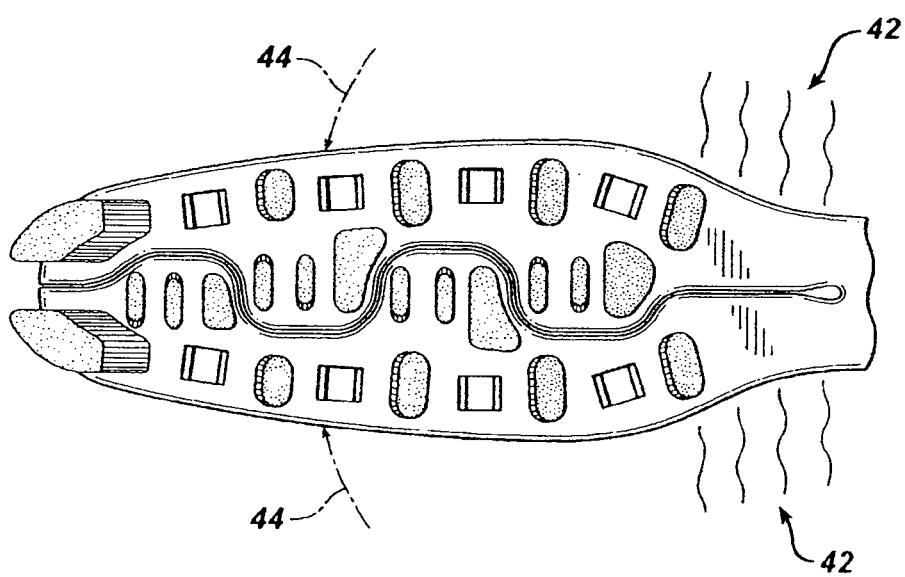
FIG. 7 is a top view of the head of FIG. 1 after the head portions have been positioned closer to each other.

With reference to FIG. 7, after the toothbrush is removed from the mold, heat 42 is applied to the head near the neck and to part of the neck (hereinafter the neck). The heat can be applied in a number of ways including hot air, radiant heating, ultrasonic or convection (e.g. hot oil) heating. Here the heat is shown being applied to the sides of the neck. It is preferable to apply the heat to the top and bottom surface of the neck. The heat brings the plastic up to 1.0-1.12 times its glass transition temperature (when temperatures are measured in the Kelvin scale). The plastic should not be heated above 1.12 times its glass transition temperature in order to avoid damaging the plastic. More preferably, the plastic is heated to about 1.03-1.06 times its glass transition temperature (measured in degrees Kelvin). The glass transition temperature for polypropylene is about 100 degrees centigrade whereas the glass transition temperature for copolyester and polyurethane is about 65 degrees centigrade.

Pressure 44 is then applied to head portions 20, 22 to move the portions towards each other. Once head portions 20, 22 are in the position shown in FIG. 2, the heated portion of the head/neck is cooled by, for example, exposing the heated portion to a cold gas or liquid. If room temperature air is used to cool the neck, such air should be applied for about 20-25 seconds. This has the effect of forming the two head portions into their final positions.

In order to achieve short process times, the highest temperature heat source which will not damage the plastic should be used. If too hot a heat source is used and/or if the heat is applied for too long, the plastic can be damaged. If the heat source is not hot enough, the process will take too long and/or head portions 20, 22 will not remain in their final desired positions. If the head/neck are made of polypropylene and hot air is used to heat the neck, (a) the heated air should be at a temperature of about 170 degrees centigrade and should be applied to the neck for about 70 seconds, (b) the polypropylene should be raised to a temperature of about 140 degrees centigrade, and (c) a nozzle which applies the hot air to the neck should be about 10 mm from the neck.

If copolyester or polyurethane is used as the material for the head neck, (a) the heated air should be at a temperature of 250 degrees centigrade and should be applied to the neck for about 10 seconds, (b) the material should be raised to a temperature of preferably 95-100 degrees centigrade, and (c) a nozzle which applies the hot air to the neck should be about 15-20 mm from the neck.

Heating the respective materials above for the time indicated allows the material to be softened and mechanically bent into its final form. Exceeding the heating times above could cause the material to overheat and become damaged.

Turning to FIGS. 8 and 9, each pivoting tuft 30 has a multiplicity of bristles 46, a base support 48 and an anchor pivot 50. The bristles are secured to and extend from a first end 52 of the base support while a first end 54 of the anchor pivot extends from a second end 56 of the base support. The base support and anchor pivot are preferably a unitary structure made of the same material. Anchor pivot 50 includes a first portion 58 near the first end 54 and a second portion 60 near a second end 62 of the anchor pivot. First portion 58 is smaller in an X an Y dimension than second portion 60. Base support 48 is larger in an X and Y dimension than second portion 60 of the anchor support. Second portion 60 includes a pair of lips 63. The anchor pivot defines an opening 64 therethrough.

Tuft 30 can also be made by a hot-tufting type process as described above. Instead of injecting plastic into the mold to form a toothbrush handle, neck and head, the plastic is injected into a mold to form base support 48 and anchor pivot 50, capturing bristles 46 when the injected plastic cools.

Figure 10:
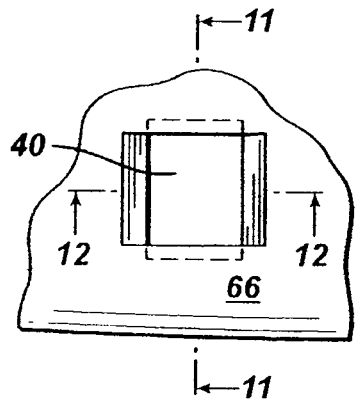
FIG. 10 is a top view of one of the holes in the head for receiving the pivoting tuft (see FIG. 6)
Figure 11:
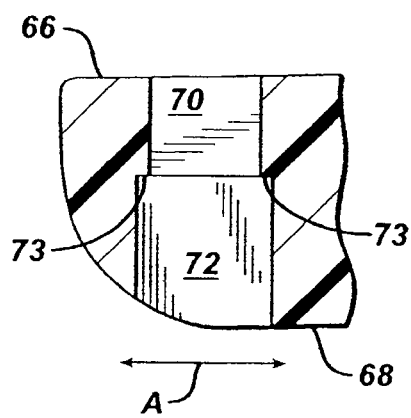
FIG. 11 is a sectional view of FIG. 10 taken along lines 11-11.
Figure 12:
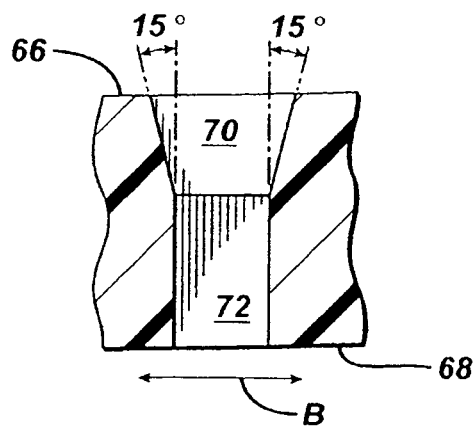
FIG. 12 is a sectional view of FIG. 10 taken along lines 12-12.

With reference to FIGS. 10-12, through holes 40 (FIG. 6) will now be described. Each hole 40 extends from a top surface 66 of the brush head through a bottom surface 68. Hole 40 includes first and second portions 70 and 72. Portion 72 is substantially a parallelepiped except that some of its lower section is rounded off (see FIG. 11). Portion 70 is also substantially a parallelepiped except that two of its sides are flared to the sides by about 15 degrees (see FIG. 12). Hole portion 72 is longer in a dimension A than hole portion 70 (FIG. 11). Hole portion 70 has about the same width in a dimension B as hole portion 72 where hole portions 70 and 72 meet (FIG. 12). Dimensions A and B are substantially perpendicular to each other in this embodiment. A pair of lips 73 are defined by this arrangement.

Figure 13:
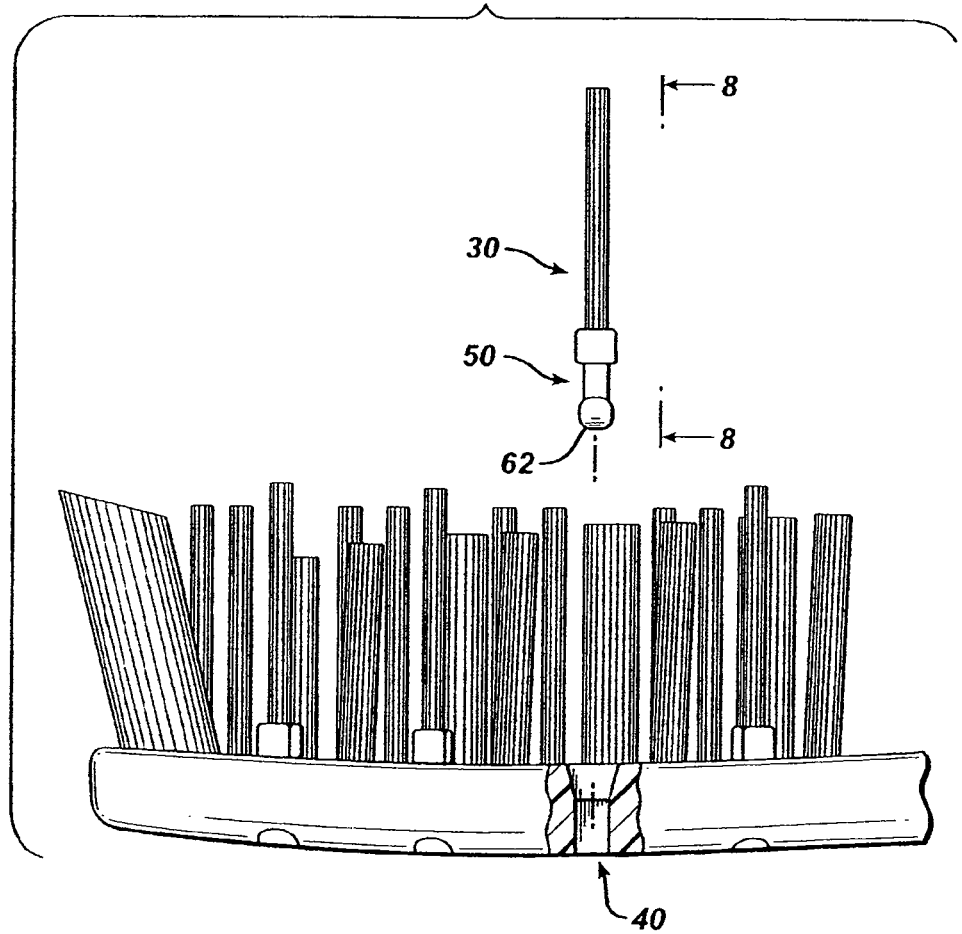
FIG. 13 is a side view of the head of FIG. 1 (a portion is removed to facilitate viewing) and a pivoting tuft prior to insertion into the head.
Figure 14:
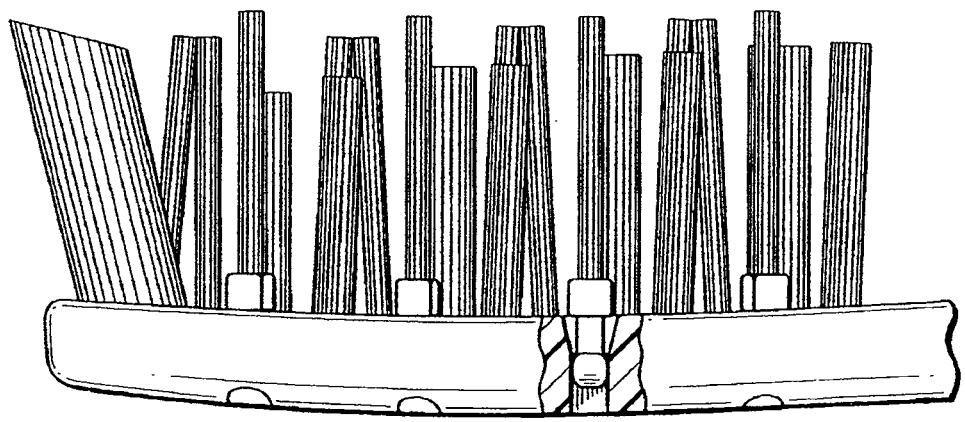
FIG. 14 is a side view of the head of FIG. 1 (a portion is removed to facilitate viewing) and a pivoting tuft after insertion into the head.

Turning now to FIGS. 13-16, the insertion of pivoting tufts 30 into holes 40 will be described. A tuft 30 is positioned over a hole 40 with end 62 of anchor pivot 50 facing the hole (FIG. 13). As shown in FIGS. 16A-C, tuft 30 is moved towards hole 40 until end 62 starts to enter the hole (FIG. 16A). Tuft 30 is then pressed into the hole causing sides of hole portion 70 to squeeze second portion 60 of the anchor pivot. Accordingly, anchor pivot 50 collapses causing opening 64 to become temporarily smaller. Tuft 30 is then pushed all the way into hole 40 (FIG. 16C) at which point the resilient plastic anchor pivot springs back to its form shown in FIG. 16A. This paragraph describes a snap-fit retention of tuft 30 to the head.

Figure 16A:
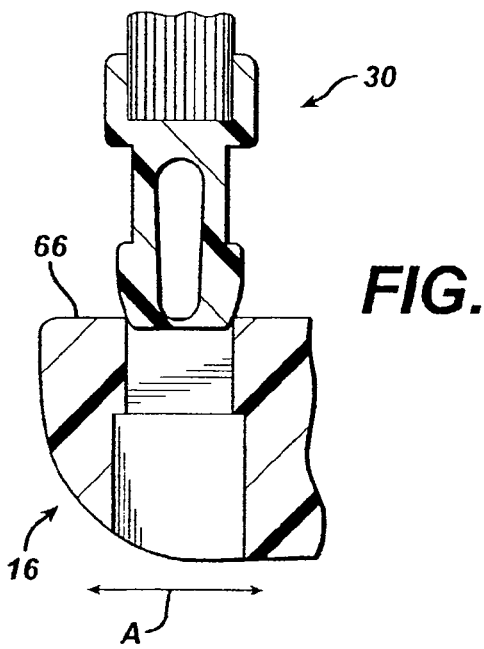
FIGS. 16A-C are sectional views of FIG. 15 taken along the lines 16A-C-16A-C.
Figure 16B:
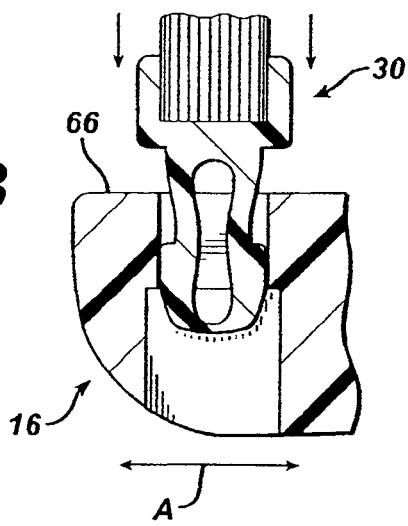
Figure 16C:
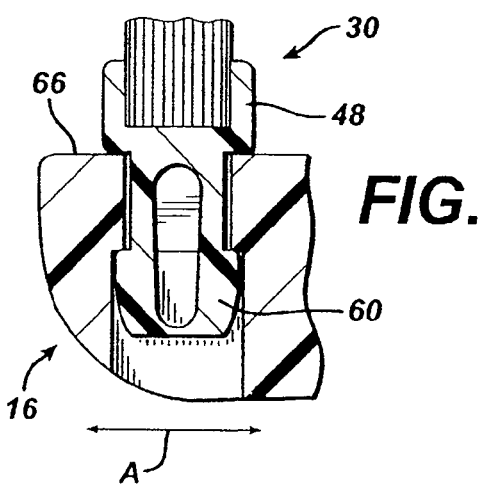

Referring to FIG. 16C, base support 48 is longer in the A dimension than hole portion 70 and thus prevents tuft 30 from being pressed further into hole 40. Second portion 60 is also longer in the A dimension than hole portion 70 and so prevents tuft 30 from moving back out of hole 40. This is due to the fact that lips 63 (FIG. 8) engage lips 73 (FIG. 11). This arrangement also prevents tuft 30 from rotating about the long axis of the bristles.

Figure 15:
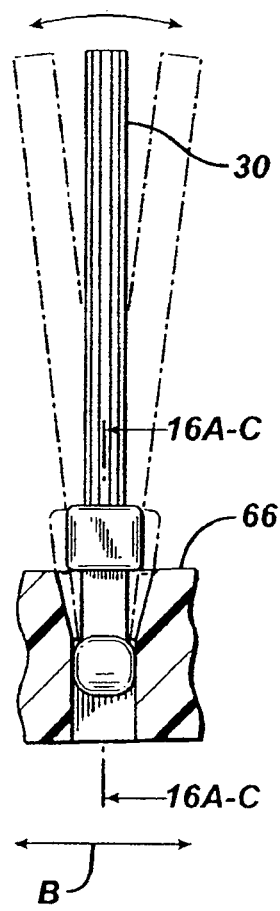
FIG. 15 is a side view of the pivoting tuft showing its motion.

As shown in FIG. 15, tuft 30 pivots when it is engaged by, for example, portions of the oral cavity during brushing. Preferably each tuft 30 can pivot up to about 15 degrees to either side of a position perpendicular to surface 66.

Figure 17:
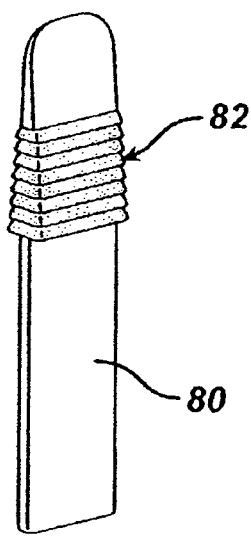
FIG. 17 is a perspective view of a tooth cleaner in the form of a ribbed fin.
Figure 18:
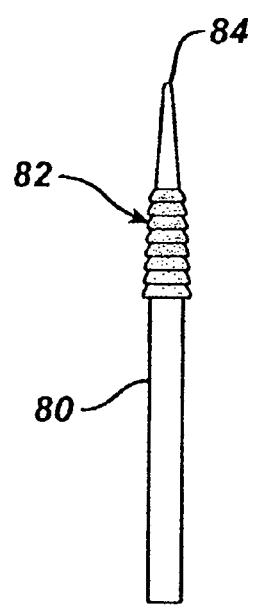
FIG. 18 is a side view of the ribbed fin of FIG. 17.

Turning to FIGS. 17 and 18, another type of tooth cleaning element in the form of a fin 80 is disclosed. Each fin is supported by a base support 48 and an anchor pivot 50 (both not shown) as described above, allowing the fin to pivot on the brush head. Alternatively, a fin can be securely affixed to the head so that it does not pivot. The fin is created of a thermoplastic elastomer (TPE) by an injection molding process. In this embodiment, a textured surface is provided by a series of ribs 82. These ribs enhance cleaning of the oral cavity. The ribs are formed by injection molding a TPE over the fin. The ribs are preferably softer than the fin. Alternative textured surfaces (e.g. dimples) can be used in place of the ribs.

As shown in FIG. 18, the fin has a width of preferably about 0.030 inches. The long dimension of the fin above the base support is preferably 0.420 inches. A tip 84 of fin 80 has a width of preferably 0.007 inches. The distance from the base of the ribs to tip 84 is about 0.168 inches whereas the distance from the top of the ribs to the tip is about 0.079 inches. The top of the ribs have a width of about 0.035 inches. The ribs (textured surface) preferably extend about 2-12 mil away from said fin.

The invention has been described with reference to a preferred embodiment. However, it will be appreciated that variations and modifications can be effected by a person of ordinary skill in the art without departing from the scope of the invention.

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A toothbrush head comprising:
    a free end, a neck, and a top surface with an opening having three or more sides and an entrance in a top surface of the head, wherein the opening has an upper portion disposed adjacent the top surface and a lower portion spaced from the top surface, wherein the upper portion of the opening has a depth which is smaller than the depth of the lower portion of the opening and wherein the upper portion has at least one side that flares away from the opening;
    a first bristle tuft extending from the top surface of the head and adjacent to the free end of the head wherein the first bristle tuft gets relatively shorter in a direction towards the neck and
    an elastomeric tooth cleaning element extending from the opening and having a base portion and a rectangular shaped cleaning portion the cleaning portion extending from the top surface of the head, wherein the elastomeric tooth cleaning element being fixed to the head such that the tooth cleaning element pivots and does not rotate; and wherein the base portion comprises a first section and a second section, wherein the second section resides in the lower section of the opening, and wherein the first section is smaller in an X and Y dimension than the second section;
    a plurality of second bristle tufts extending from the top surface of the head having a length that is less than the length of the elastomeric element;
    wherein the opening and the elastomeric tooth cleaning element are located adjacent a perimeter of the head such that a tip of the cleaning portion does not extend beyond an outside edge of the head.

2. The toothbrush head according to claim 1, wherein the upper portion of the opening and the lower portion of the opening have different cross-sections.

3. The toothbrush head according to claim 1, wherein at least one of the upper portion and lower portion is substantially a parallelepiped.

4. The toothbrush head according to claim 1, wherein the cleaning portion has a width of less than about 0.03 inches.

5. The toothbrush head according to claim 1, wherein the first section and the second section meet and form a pair of base section lips.

6. The toothbrush head according to claim 1, wherein the upper portion and the lower portion meet and form a pair of lips.

7. The toothbrush head according to claim 1 wherein the top portion flares away from the opening by at least about 15 degrees.

8. The toothbrush head according to claim 1 wherein the toothbrush head comprises a length and a width and wherein the length is substantially longer than the width.

9. The toothbrush head according to claim 1 wherein the toothbrush head further comprises a plurality of second bristle tufts and wherein the plurality of second bristle tufts have a length that is less than the length of the elastomeric tooth cleaning element.

10. The toothbrush head according to claim 9 wherein the length of the plurality of second bristle tufts is less than the length of the first bristle tuft.

11. The toothbrush head according to claim 1 wherein the first bristle tuft forms an acute angle with the top surface of the head.

12. The toothbrush head according to claim 1 wherein the elastomeric tooth cleaning element has a textured surface formed from a plurality of ribs.

13. The toothbrush head according to claim 12 wherein the ribs are softer than the elastomeric tooth cleaning element.

14. The toothbrush according to claim 1 further comprising a plurality of third bristle tufts wherein the third bristle tufts extend from the top surface of the head and are in a center portion the head.

* * * * *